(12) United States Patent
Bobrow et al.

(10) Patent No.: US 6,372,937 B1
(45) Date of Patent: Apr. 16, 2002

(54) ENHANCED CATALYZED REPORTER DEPOSITION

(76) Inventors: Mark Norman Bobrow, 11 Battle Green Rd., Lexington, MA (US) 02421; Karl Edwin Adler, 2 Shandel Dr., Newburyport, MA (US) 01950; Kevin Aaron Roth, 526 Webster Forest, Webster Groves, MO (US) 63119

( * ) Notice: Subject to any disclaimer, the term of this patent is extended or adjusted under 35 U.S.C. 154(b) by 0 days.

(21) Appl. No.: 09/434,742

(22) Filed: Nov. 5, 1999

Related U.S. Application Data

(60) Provisional application No. 60/107,654, filed on Nov. 9, 1998.

(51) Int. Cl.[7] ................ C07C 229/00; C07C 233/00
(52) U.S. Cl. ........................... 562/444; 564/167
(58) Field of Search ............... 562/444; 564/167

(56) References Cited

U.S. PATENT DOCUMENTS

| | | | |
|---|---|---|---|
| 4,521,511 A | 6/1985 | Stout ........................... 435/28 |
| 4,598,044 A | 7/1986 | Kricka et al. ................. 435/28 |
| 4,729,950 A | 3/1988 | Kricka et al. ................. 435/28 |
| 4,835,101 A | 5/1989 | Kao et al. ..................... 435/28 |
| 5,196,306 A | 3/1993 | Bobrow et al. ............. 435/7.9 |
| 5,583,001 A | 12/1996 | Bobrow et al. ............. 435/7.5 |
| 5,629,168 A | 5/1997 | Kricka ......................... 435/28 |
| 5,688,966 A | 11/1997 | Bobrow et al. ............. 548/455 |
| 5,731,158 A | 3/1998 | Bobrow et al. ............. 435/7.5 |
| 5,767,287 A | 6/1998 | Bobrow et al. ............. 548/455 |
| 5,863,748 A | 1/1999 | Bobrow ....................... 435/28 |

OTHER PUBLICATIONS

Rama et al, studies directed towards the total synthesis of vancomycin, Tetrahedron Letters (1994), 35 (45), 8465–8468, 1994.*
Resmini et al, preparation by PH–dependence and chemical modification studies, Biochem. J. (1997), 326 (1), 279–287, 1997.*
Tacker et al. (1972) Effect of tranylcypromine sulphate on the metabolism of [14C] tyramine in vivo in the rat. Journal of Pharmacy and Pharmacology, vol. 24, No. 3, pp. 245–246.
Tanaka et al. (1980) Gas–chromatographic method of analysis for urinary organic acids. I. Retention indices of 155 metabolically important compounds. Clinical Chemistry, vol. 26, No. 13, pp. 1839–1846.
Bobrow et al. (1989) Catalyzed reporter deposition, a novel method of signal amplification. Application to immunoassays. Journal of Immunological Methods, 125:279–285.

Bobrow et al. (1991) Catalyzed reporter deposition, a novel method of signal amplication. II. Application to membrane immunoassays. Journal of Immunological Methods, 137:103–112.
deJong et al. (1985) Sensitivity of various visualization methods for peroxidase and alkaline phosphatase activity in immunoenzyme histochemistry. Histochemical Journal, vol. 17, pp. 1119–1130.
Straus (1982) Imidazole increases the sensitivity of the cytochemical reaction for peroxidase with diaminobenzidine at at neutral pH. Journal of Histochemistry and Cytochemistry, vol. 30, pp. 491–493.
Whitaker and Tappel (1962) Modifification of enzyme activity. II Effect of salts on α–amylase, alcohol dehydrogenase, peroxidase and hematin catalysis. Biochimica et Biophysica Acta., vol. 62, pp. 310–317.

* cited by examiner

*Primary Examiner*—Johann Richter
*Assistant Examiner*—J. Parsa
(74) *Attorney, Agent, or Firm*—Gifford, Krass, Groh, Sprinkle, Anderson & Citkowski, P.C.

(57) ABSTRACT

A method for enhancing the conversion of a phenol substrate to a product by a peroxidase enzyme comprises the steps of reacting a conjugate comprising a detectably labeled phenol with a peroxidase enzyme in the presence of an enhancing reagent, the enhancing reagent conmprising an inorganic salt, an organic compound having the formula

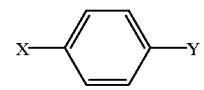

wherein when X is $B(OH)_2$, Y is I, or wherein when X is OH, Y is a halogen, or Q-R wherein Q is a linear or branched 1–12 heteroatom alkyl wherein the heteroatoms are selected from C, N, O, and S, wherein the bonds connecting the heteroatom alkyl chain are single or double, wherein any carbon atom in the heteroatom alkyl chain optionally includes a substituent selected from —OH, —COOH, —$NH_2$, and —SH, and wherein R is selected from —OH, —COOH, —$NH_2$, and —$CH_3$; or mixtures of the inorganic salt and the organic compound. A compound having the formula:

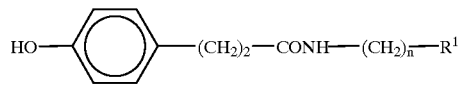

wherein $R^1$ is —$CH_2OH$, —COOH, and n is 1–8.

7 Claims, 4 Drawing Sheets (4 of 4 Drawing Sheet(s) Filed in Color)

ENHANCED CATALYZED REPORTER DEPOSITION

RELATED APPLICATION

This application claims priority of U.S. Provisional Application Serial No. 60/107,654 filed Nov. 9, 1998.

FIELD OF THE INVENTION

This invention relates to enzymatic assays, and more particularly to enhancing the reactivity of peroxidase for use in catalyzed reporter deposition.

BACKGROUND OF THE INVENTION

Peroxidase, because of its high turnover rate, good stability, and availability is widely used in enzyme-based analytical methods. For example, horseradish peroxidase (HRP) (EC 1.11.1.7) catalyzes the oxidation of a large variety of hydrogen-donating substrates with hydrogen peroxidase. HRP is also one of the preferred enzymes for use in catalyzed reporter deposition.

Catalyzed reporter deposition (CARD) is a novel method of signal amplification which constitutes the subject matter of U.S. Pat. Nos. 5,863,748; 5,688,966; 5,767,287; 5,731,158; 5,583,001 and 5,196,306 all of which are incorporated herein by reference. It is also discussed in Bobrow et al., *Journal of Immunological*, 125: 279–285 (1989) and in Bobrow et al., *Journal of Immunological Methods*, 137: 103–112 (1991).

The method utilizes an analyte-dependent enzyme activation system ("ADEAS") to catalyze the deposition of a detectable label onto the solid phase of an assay platform. These enzymatically deposited labels may be detected directly or indirectly and results in signal amplification and improved detection limits. In a preferred embodiment, HRP is the enzyme.

HRP reacts with a conjugate consisting of a detectably labeled substrate specific for the ADEAS. When the ADEAS and the conjugate react, an activated conjugate is formed which deposits covalently wherever receptor site for the activated conjugate is immobilized.

For analytical use, substrate oxidation by HRP has been used to generate products which become colored, fluorescent or chemiluminescent. These products either remain soluble or become insoluble and precipitate on the solid phase. The CARD method differs in this respect as the products of the detectably labeled phenol substrate become covalently bound to the solid phase.

To improve detection limits in analytical methods, it is desirous to increase or enhance the substrate to product conversion by enzymes. Although a substance which enhances HRP catalysis regardless of the substrate used has not been discovered, several enhancers specific for HRP substrates which form soluble products have been described. One enhancer specific for the substrate diaminobenzidine, which forms an insoluble product has been described. Enhancers for substrates which, by the catalytic activity of HRP, form covalently depositable products have not been described.

J. R. Whitaker and A. L. Tappel, *Biochirnica et Biophysica Acta*, pages 310–317, Vol. 62, 1962 show that KCl, NaCl, Na$_2$SO4 and to a lesser extent, LiCl enhance the oxidation of guaiacol.

U.S. Pat. No. 4,598,044 issued to Kricka et al. on Jul. 1, 1986 describes the enhancement of the HRP catalyzed oxidation of the substrate, 2,3-dihydro-1,4-phthalazinedione, which forms a soluble chemiluminescent product, by various phenolic compounds.

U.S. Pat. No. 4,729,950 issued to Kricka et al. on Mar. 8, 1988 describes the enhancement of the HRP catalyzed oxidation of the substrate, 2,3-dihydro-1,4-phthalazinedionc, by various aromatic amine compounds. Tables 1 and 2 summarize various substrate/enhancer combinations. The Tables and the discussion (column 3 line 67 to column 4 line 34) lead to the conclusion that whether an HRP catalyzed oxidation of a substrate will be enhanced by a given compound is not predictable.

U.S. Pat. No. 5,629,168 issued to Kricka on May 13, 1997 describes the enhancement of the HRP catalyzed oxidation of the substrate, 2,3-dihydro-1,4-phthalazinedione, by aromatic organoboron compounds.

U.S. Pat. No. 4,521,511 issued to Stout on Jun. 4, 1985 describes the enhancement of the HRP catalyzed oxidation of the substrate, 2,2'-azino-di(3-ethyl-benzothiazolone-6-sulfonic acid), by various phenolic compounds.

W. Straus, *Journal of Histochemistry and Cytochemistry*, Vol. 30, pages 491–493, 1982, shows that imidazole enhances the HRP catalyzed oxidation of diaminobenzidine which forms in insoluble product. p A. S. H. de Jong et al., *Histochemical Journal*, Vol. 17, pages 1119–1130, 1985 also show that imidazole enhances the oxidation of diaminobenzidine by approximately four fold, a substrate combination of p-phenylenediamine-pyrocatechol by two fold and has no effect on the substrate 4-chloro-1-naphthol, all of which form insoluble products.

The aforementioned enhancers, with the exception of imidazole, only enhance the conversion of soluble substrates to soluble products. In addition, the enhancers are substrate specific. The KCl, NaCl, Na$_2$SO$_4$ and LiCl enhancement of the oxidation of guaiacol is specific for guaiacol. These salts do not enhance the oxidation of substrates which form insoluble products nor do they enhance the oxidation of commonly used substrates that form soluble products, such as oi hophenylcdiamine or tetramethylbenzidine. The enhancers for 2,3-dihydro-1,4-phthalazinedione also do not enhance the oxidation of substrates which form insoluble products nor do they enhance the oxidation of commonly used substrates that form soluble products, such as ortho-phenylediamine or tetramethylbenzidine. Imidazole, which has been demonstrated to enhance the oxidization of diaminobenzidine, has a marginal effect on p-phenylenediamine-pyrocatechol, no effect on 4-chloro-1-naphthol, and no effect on substrates which form covalently depositable products. Whether the oxidation of a given substrate by HRP will be enhanced by a given compound cannot be predicted.

Accordingly, it would be advantageous and desirable to have reagents for enhancing the catalysis of HRP and to have an enhancement effect greater than would be expected based on previous technology.

SUMMARY OF THE INVENTION

The present invention concerns enhancing the catalysis of HRP in a Catalyzed Reporter Deposition (CARD) method by reacting a conjugate comprising a detectably labeled phenol with a peroxidase enzyme, wherein the reaction is carried out in the presence of an enhancing reagent including at least one inorganic salt, an organic enhancing compound or mixtures of both the inorganic salt and the organic enhancing reagents of the structure,

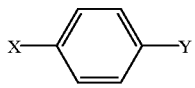

wherein when X is B(OH)$_2$, Y is I; or wherein when X is OH, Y is a halogen, or Q-R, wherein Q is a linear or branched 1–12 heteroatom alkyl chain, wherein the heteroatoms can be selected from C, N, O and S, wherein the bonds connecting the alkyl chain are single or double, wherein any carbon in the alkyl chain optionally includes a substituent selected from —OH, —COOH, —NH$_2$, and —SH, and wherein R is selected from —OH, —COOH, —NH$_2$, and —CH$_3$.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other advantages of the present invention will be readily appreciated as the same becomes better understood by reference to the following detailed description when considered in connection with the accompanying drawings wherein.

DETAILED DESCRIPTION OF THE INVENTION

Figure 1A:
FIG. 1A–C are photographs illustrating the results of Enhanced Catalyzed Reporter Deposition (CARD) detection wherein (A) is a photograph illustrating the results of standard CARD detection using cyanine 3 tyramide, (B) is a photograph illustrating the results of organic enhanced CARD detection using cyanine 3 tyramide, and (C) is a photograph illustrating the results of organic and salt enhanced CARD detection using cyanine 3 tyramide.

The present invention relates to enhancing the catalysis of HRP in a CARD or tyramide signal amplification (TSA) method by reacting a conjugate comprising a detectably labeled phenol with a peroxidase enzyme, wherein the reaction is carried out in the presences of an enhancing reagent which includes at least one inorganic salt such as NaCl, MgCl$_2$, KCl, CaCl$_2$, sodium phosphate, sodium acetate, ammonium acetate and ammonium sulfate, an organic enhancing compound or mixtures of both the inorganic and the organic enhancing reagents.

Organic compounds useful as enhancing reagents are of the structure

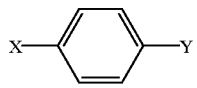

wherein when X is B(OH)$_2$, Y is I; or wherein when X is OH, Y is a halogen, or Q-R, wherein Q is a linear or branched 1–12 heteroatom alkyl chain, wherein the heteroatoms are selected from C, N, O and S, wherein the bonds connecting the alkyl chain are single or double, wherein any carbon in the alkyl chain optionally includes a substituent selected from —OH, —COOH, —NH$_2$, —SH, and wherein R is selected from —OH, —COOH, —NH$_2$, and —CH$_3$.

Broadly, the concentration of the inorganic enhancing reagent ranges from approximately 0.1 M to saturation. The concentration of the inorganic enhancing reagent preferably is at least approximately 0.5 M. Most preferably, the concentration of the inorganic enhancing reagent ranges from approximately at least 2 M to saturation.

The concentration of the organic enhancing reagent preferably ranges between approximately $1\times10^{-7}$ M and $1\times10^{-3}$ M. More preferably, the concentration of the organic enhancing reagent ranges from approximately $1\times10^{-6}$ M to $1\times10^{-4}$ M.

Preferred organic enhancing reagents include compounds of the structures

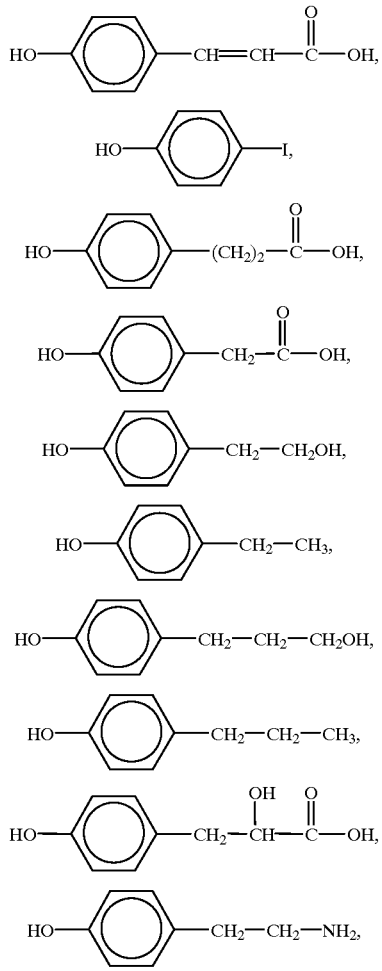

-continued

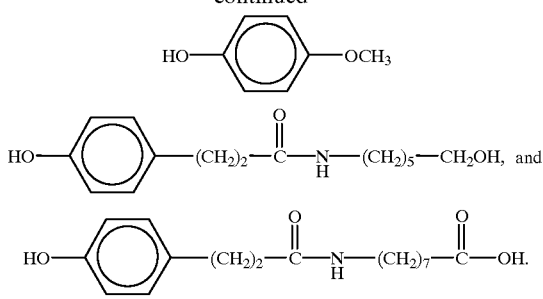

For use with non-fluorescent reagents,

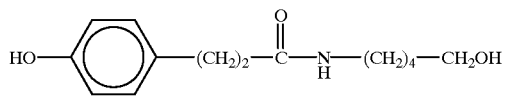
(1)

is the most preferred enhancer. When a fluorescent substrate is utilized,

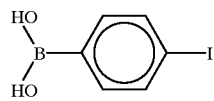
(2)

is the most preferred enhancer.

As used herein, the term conjugate means a detectably labeled phenol which is a substrate for the HRP enzyme. Preferred conjugates include tyramide compounds, p-hydroxycinnanic acid and derivatives thereof. The conjugate therefore comprises two components. One component is the phenol moiety which serves as the substrate for the enzyme. The other component is the detectable label.

As used herein, detectably labeled means that the substrate can be coupled to either a reporter or to an unlabeled first member of a specific binding pair. When the substrate is coupled to an unlabeled member of a specific binding pair, following covalent binding of the activated conjugate, the substrate-specific binding pair complex is reacted with the second member of the binding pair which is coupled to a reporter.

As used herein, the term receptor site means a site at which the activated conjugate will bind to the surface through the formation of a covalent bond. Examples of receptor site compositions for phenolic substrates include tyrosine residues of proteins, phenol and other electron rich organic molecules. The receptor sites may be reactive components of the surface of a solid support or may be added to the surface of the solid support.

As used herein, the term activated conjugate means the conjugate has been primed to bind to the receptor site.

As used herein, the term halogen includes chlorine, fluorine, bromine, and iodine.

As used herein, the term alkyl means a straight or branched chain hydrocarbon. Representative examples of alkyl groups are methyl, ethyl, propyl, isopropyl, isobutyl, butyl, tert-butyl, sec-butyl, pentyl, and hexyl.

As used herein, the term heteroatom includes oxygen, nitrogen, and sulfur.

Members of specific binding pairs suitable for use in practicing the invention can be of the immune or non-immune type. Immune specific binding pairs are exemplified by antigen/antibody systems or hapten/anti-hapten systems. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab type fragments which are defined as fragments devoid of the Fe portion, e.g., Fab, Fab' and F(ab')2 fragments, or may be so-called half molecule fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immmune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino) benzoic acid (DMAB), etc.

As used herein, the term enhancing reagent means a reagent which increases or accelerates the rate of binding of the activated conjugate to the receptor site. The increased or accelerated binding of the activated conjugate to the receptor site is monitored directly or indirectly from the detectable label of the conjugate.

The present invention is surprising and unexpected because of the molecular nature of the enhancer moieties in relation to the detectably labeled substrate. Two reactions are required to allow the conjugate to bind to the receptor site. First, the peroxidase enzyme catalyzes the oxidation, or activation of the conjugate; second, the activated conjugate reacts with the receptor site, forming a covalent bond. The structures of the organic enhancers lend themselves as substrates for HRP and/or receptor sites for the activated conjugate. Therefore, one would predict that these moieties would act as inhibitors of either the first, the second, or both reactions rather than as enhancers.

It is also surprising that the inorganic and organic enhancers of the instant invention when combined are additive in their enhancement effect.

Example 1

Enhanced Catalyzed Reporter Deposition (CARD) Detection Using Cyanine 3 Tyramide Human prostate tissue slides (Dako Corp., Carpinteria, Calif.) were deparaffinized and blocked for thirty minutes with TNB Blocking Buffer (TSA Direct Cyanine 3 kit, NEN Life Science Products, Boston, Mass.). Rabbit anti-human prostate specific antigen (Dako) diluted 1/40,000 in TNB buffer was incubated for one hour at room temperature. The slides were washed in TNT buffer (TSA Direct Cyanine 3 kit) and then incubated with an anti-rabbit IgG-HRP conjugate (Roche Molecular Biochemicals, Indianapolis, Ind.) diluted 1/1000 in TNB buffer for one hour at room temperature.

Standard CARD detection was performed using the TSA Direct Cyanine 3 kit. Organic enhanced CARD detection was performed using the TSA Direct Cyanine 3 kit and adding p-iodophenyl boronic acid (structure 2) at a 20:1 (w/w) ratio to the cyanine 3 tyramide reagent. Organic and salt enhanced CARD detection was performed using the TSA Direct Cyanine 3 kit, adding p-iodophenyl boronic acid (structure 2) at a 20:1 (w/w) ratio to the cyanine 3 tyramide reagent and adding NaCl to the diluent to a final concentration of 2M.

The slides were washed in TNT buffer, mounted with mounting medium and a coverslip.

Figure 1B:
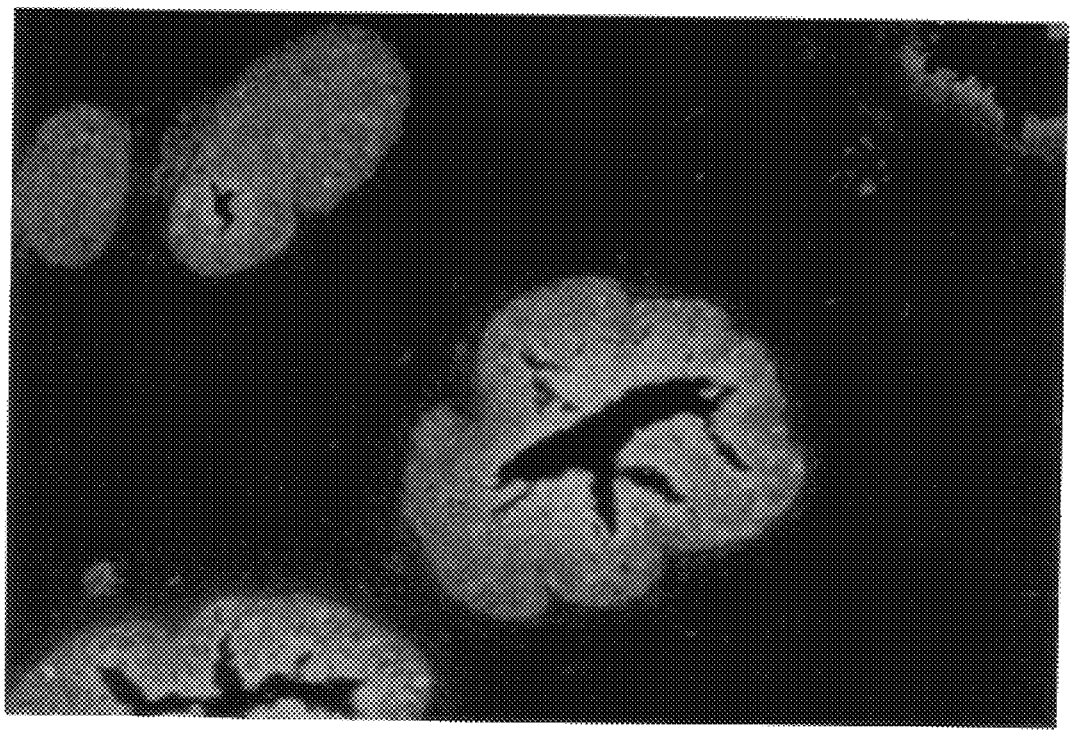
Figure 1C:
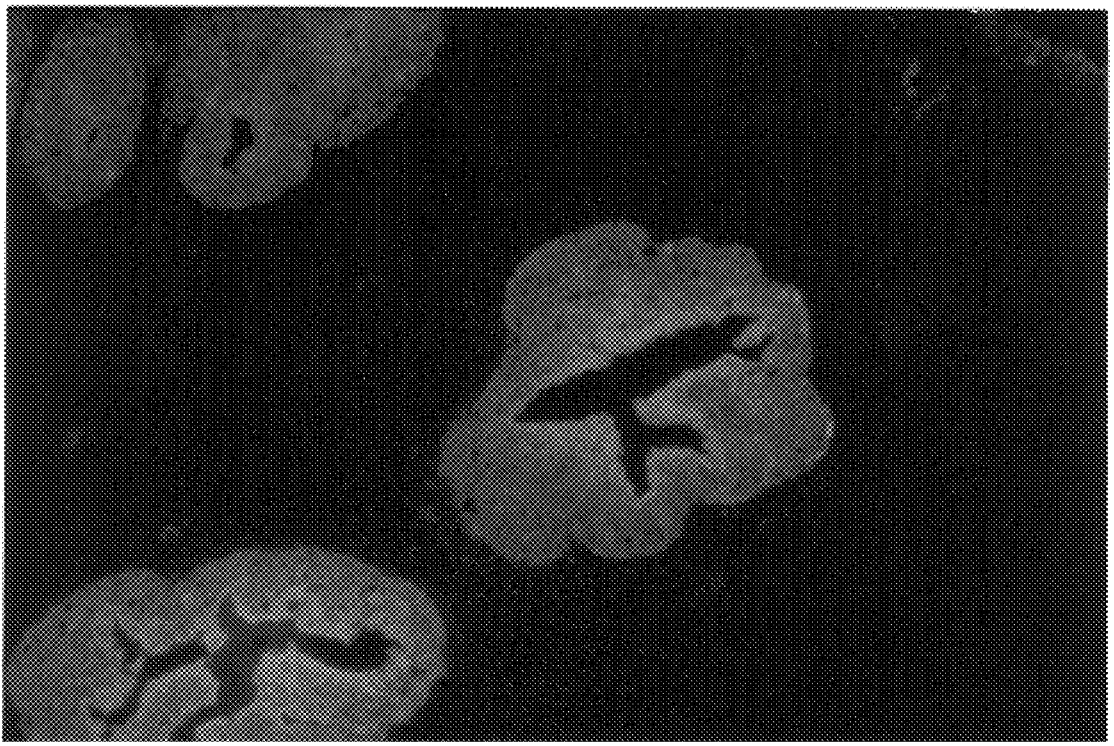

FIG. 1A shows the results of standard CARD detection using cyanine 3 tyramide. FIG. 1B shows the results of organic enhanced CARD detection using cyanine 3 tyramide. FIG. 1C shows the results of organic and salt enhanced CARD detection using cyanine 3 tyramide. There is a very dramatic difference between the standard and organic enhanced cyanine 3 detection (FIG. 1A compared to FIG. 1B) showing the improved detection. There is an unexpected and significant improvement on the addition of salt to the organic enhanced cyanine 3 detection (FIG. 1B compared to FIG. 1C). The difference is more obvious when seen visually as compared to photographically.

EXAMPLE 2

Enhanced Catalyzed Reporter Deposition (CARD) Detection Using Fluorescein Tyramide Human prostate tissue slides (Dako) were deparaffinized and blocked for thirty minutes with TNB Blocking Buffer (TSA Direct Green kit, NEN Life Science Products). Rabbit anti-human prostate specific antigen (Dako) diluted 1/10,000 in TNB buffer was incubated for one hour at room temperature. The slides were washed in TNT buffer (TSA Direct Green kit) and then incubated with an anti-rabbit IgG-HRP conjugate (Roche) diluted 1/1000 in TNB buffer for one hour at room temperature.

Standard CARD detection was performed using the TSA Direct Green kit, which utilizes fluorescein tyramide. Organic enhanced CARD detection was performed using the TSA Direct Green kit and adding p-iodophenyl boronic acid (structure 2) at a 20:1 (w/w) ratio to the fluorescein tyramide reagent. Organic and salt enhanced CARD detection was performed using the TSA Direct Green kit, adding p-iodophenyl boronic acid (structure 2) at a 20:1 (w/w) ratio to the fluorescein tyramide reagent and adding NaCl to the diluent to a final concentration of 2M.

The slides were washed in TNT buffer, mounted with mounting medium and a coverslip.

Figure 2A:
FIG. 2A–C are photographs illustrating Enhanced Catalyzed Reporter Deposition (CARD) detection using fluorescein tyramide wherein (A) illustrates the results of standard CARD detection using fluorescein tyramide, (B) illustrates the results of organic enhanced CARD detection using fluorescein tyramide, and (C) shows the results of organic and salt enhanced CARD detection using fluorescein tyramide.
Figure 2B:
Figure 2C:
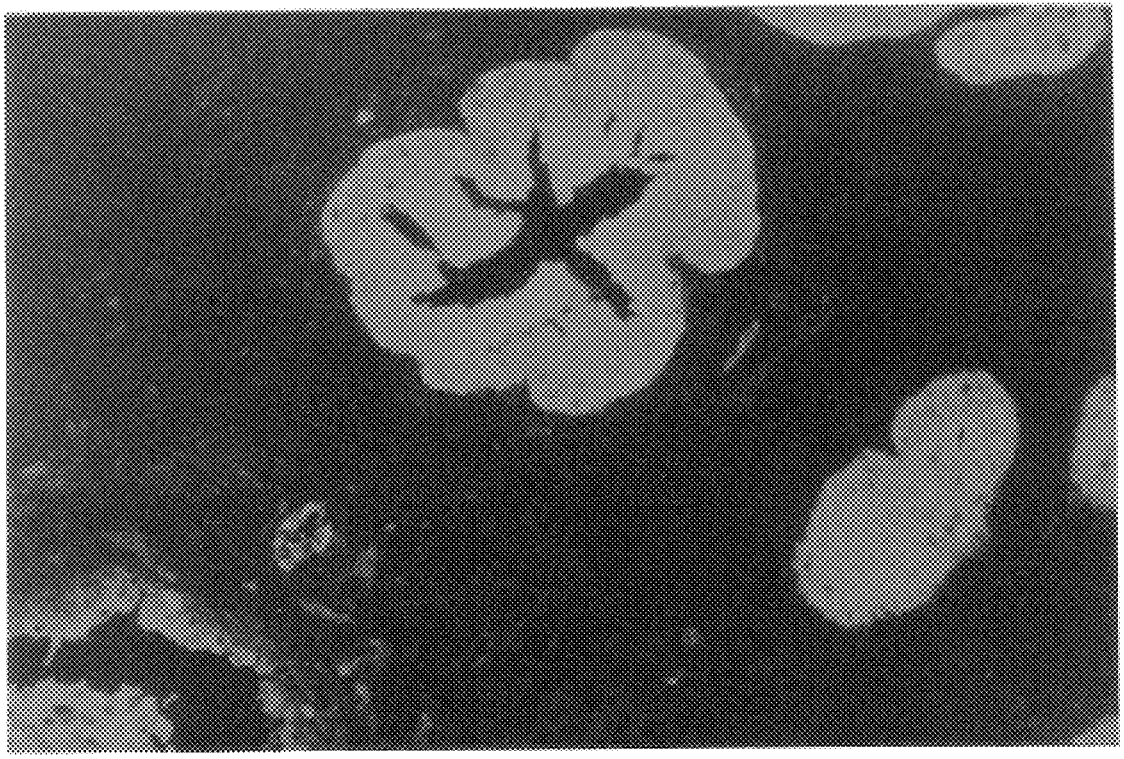

FIG. 2A shows the results of standard CARD detection using fluorescein tyramide. FIG. 2B shows the results of organic enhanced CARD detection using fluorescein tyramide. FIG. 2C shows the results of organic and salt enhanced CARD detection using fluorescein tyramide. There is significant difference between the standard and organic enhanced fluorescein detection (FIG. 2A compared to FIG. 2B) showing the improved detection. There is an unexpected and very dramatic improvement on the addition of salt to the organic enhanced fluorescein detection (FIG. 2B compared to FIG. 2C). Comparing the differences between organic and salt enhancement between the cyanine 3 tyramide substrate (Example 1) and the fluorescein tyramide substrate in this example demonstrates the lack of predictability and unexpected result of the enhancement effect.

EXAMPLE 3

Enhanced Catalyzed Reporter Deposition (CARD) Detection Using Biotinyl Tyramide

Human prostate tissue slides (Dako) were deparaffinized and blocked for thirty minutes with TNB Blocking Buffer (TSA Indirect kit, NEN Life Science Products). Rabbit anti-human prostate specific antigen (Dako) diluted 1/100,000 in TNB buffer was incubated for one hour at room temperature. The slides were washed in TNT buffer (TSA Indirect kit) and then incubated with an anti-rabbit IgG-HRP conjugate (Roche) diluted 1/1000 in TNB buffer for one hour at room temperature.

Standard CARD detection was performed using the TSA Indirect kit, which utilizes biotinyl tyramide. Organic and salt enhanced CARD detection was performed using the TSA Indirect kit, adding N-(5-hydroxypentyl)-3-(p-hydroxyphenyl)propionamide (structure 1) at a 20:1 (w/w) ratio to the biotinyl tyramide reagent and adding NaCl to the diluent to a final concentration of 2M. The slides were washed in TNT buffer, and Streptavidin-HRP (TSA Indirect kit) diluted 1/100 in TNB buffer was incubated for thirty minutes at room temperature. The slides were washed in TNT buffer and diaminobenzidine (NEN Life Science Products) was added and incubated for three minutes at room temperature. The slides were washed with water, and counterstained with Hematoxylin. The slides were then washed with water, phosphate buffered saline, water, dehydrated and mounted.

Figure 3A:
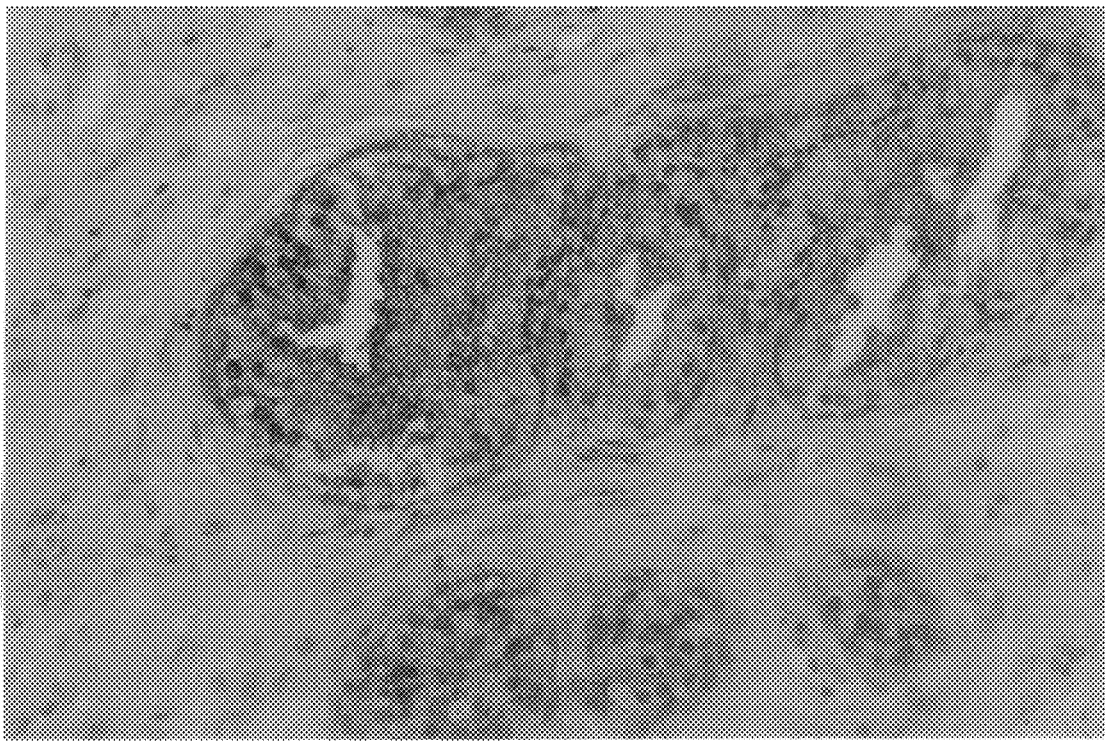
FIG. 3A–B illustrate the enhanced of Enhanced Catalyzed Reporter Deposition (CARD) detection using biotinyl tyramide wherein (A) shows the results of standard CARD detection using biotinyl tyramide, and (B) shows the results of organic and salt enhanced CARD detection using biotinyl tyramide.
Figure 3B:
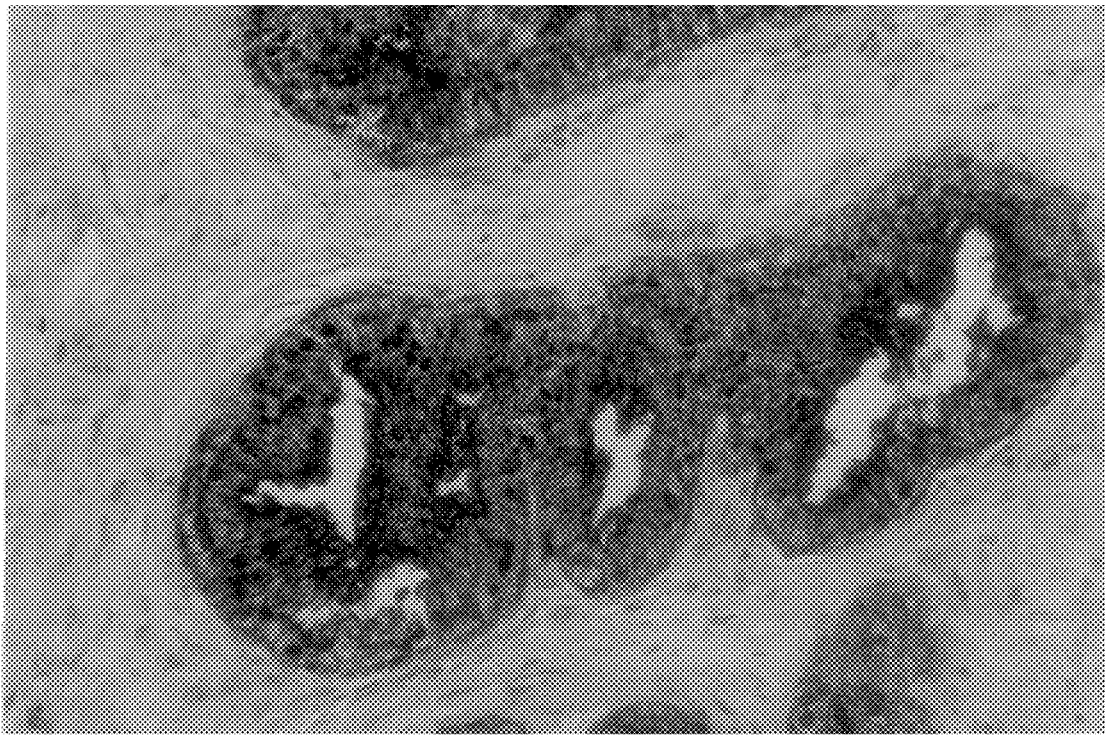

FIG. 3A shows the results of standard CARD detection using biotinyl tyramide. FIG. 3B shows the results of organic and salt enhanced CARD detection using biotinyl tyramide. There is a striking difference between the standard and enhanced biotinyl tyramide detection (FIG. 3A compared to FIG. 3B) showing the improved detection.

The foregoing drawings, discussion and description are illustrative of the general principles of the present invention, and some specific embodiments thereof, but are not meant to be limitations upon the practice of the present invention, since numerous modifications and variations will be readily apparent to one of skill in the art. It is the following claims, including all equivalents, which define the scope of the invention.

What is claimed is:

1. A compound having the formula:

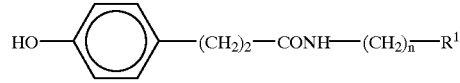

wherein $R^1$ is —$CH_2OH$, —COOH, and n is 4, 5, or 7.

2. A compound according to claim 1, wherein $R^1$ is —$CH_2OH$.

3. A compound according to claim 1, wherein n is 4 and $R^1$ is —$CH_2OH$.

4. A compound according to claim 1, wherein n is 5 and $R^1$ is —$CH_2OH$.

5. A compound according to claim 1, wherein n is 7 and $R^1$ is —COOH.

6. A compound having the formula:

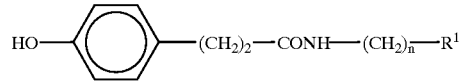

wherein $R^1$ is —$CH_2OH$, and n is 1–8.

7. A compound having the formula:

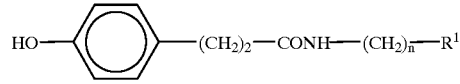

wherein $R^1$ is —$CH_2OH$, —COOH, and n is 4–8.

* * * * *